United States Patent [19]

Black et al.

[11] 4,238,497
[45] Dec. 9, 1980

[54] IMIDAZOLINE DERIVATIVES, SALTS THEREOF AND THEIR USE AS PESTICIDES

[75] Inventors: Malcolm H. Black, Tring; Alexander D. Frenkel, Aston Clinton; Peter T. Roberts, Berkhamsted, all of England

[73] Assignee: Burroughs Wellcome Co., Research Triangle Park, N.C.

[21] Appl. No.: 954,745

[22] Filed: Oct. 26, 1978

[30] Foreign Application Priority Data

Oct. 26, 1977 [GB] United Kingdom ............... 44486/77

[51] Int. Cl.³ .................... C07D 233/20; A61K 31/45
[52] U.S. Cl. ................................ 424/273 R; 548/352; 548/353
[58] Field of Search ............................. 548/352, 353; 424/273 R

[56] References Cited

U.S. PATENT DOCUMENTS

| 4,000,079 | 12/1976 | Rasp et al. ............................ 548/353 |
| 4,013,776 | 3/1977 | Lafon .................................. 548/353 |

FOREIGN PATENT DOCUMENTS 51-106739  9/1976  Japan.

Primary Examiner—Henry R. Jiles
Assistant Examiner—Jane T. Fan
Attorney, Agent, or Firm—Donald Brown

[57] ABSTRACT

Imidazoline compounds of formula (I):

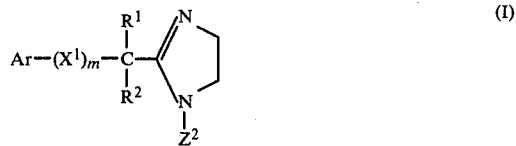

wherein
Ar is selected from a phenyl or a mono-, di- or tri-substituted phenyl radical in which the substituents are selected from alkyl, alkoxy, halogen, hydroxy, cyano, amino, trihalomethyl and nitro and in which any two adjacent carbon atoms of the phenyl ring may be joined by a carbon chain containing 3 or 4 carbon atoms;
$X^1$ is S, $NR^3$ or $NZ^1$;
$R^1$ and $R^2$ are selected from hydrogen or alkyl;
$R^3$ is alkyl or aryl;
m is 0 or 1; and
$Z^1$ and $Z^2$ are a group $SO_nR^9$ or a group

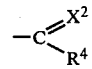

in which $X^2$ is O, S or $NR^5$;
$R^4$ is alkyl, aryl, alkoxy, aryloxy, amino or amido;
$R^5$ is alkyl, aryl, alkoxy, aryloxy, alkylthio, arylthio, amino or amido;
the alkyl or alkoxy radicals containing from 1 to 4 carbon atoms each; or an acid addition salt of the imidazoline compound.

Methods of preparing the compounds are provided, as are pesticidal formulations containing them.

The compounds are active against pests, especially arthropods of the Order Acarina.

23 Claims, No Drawings

IMIDAZOLINE DERIVATIVES, SALTS THEREOF AND THEIR USE AS PESTICIDES

This invention relates to imidazolines, their preparation and intermediates therefor, pesticidal formulations containing the imidazolines, and to their use as pesticides.

We have found that compounds of formula (I) below and their acid addition salts have activity against Arthropods, in particular against members of the Order Acarina.

The Compounds of formula (I) are:

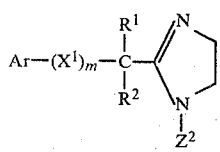
(I)

wherein
- Ar is a phenyl or a mono-, di- or tri-substituted phenyl radical in which the substituents may be the same or different and are selected from alkyl, alkoxy, halogen, hydroxy, cyano, amino, trihalomethyl and nitro and in which any two adjacent, otherwise unsubstituted, carbon atoms of the phenyl ring may together be joined by a carbon chain containing 3 or 4 carbon atoms;
- $X^1$ is S, $NR^3$ or $NZ^1$;
- $R^1$ and $R^2$ may be the same or different and are selected from hydrogen or alkyl;
- $R^3$ is alkyl or aryl;
- m is 0 or 1; and
- $Z^1$ and $Z^2$ may be the same or different and are a group $-SO_nR^9$ or a group

in which $X^2$ is O, S or $NR^5$;
- $R^4$ is alkyl, aryl, alkoxy, aryloxy or $NR^6R^7$;
- $R^5$ is alkyl, aryl, alkoxy, aryloxy, alkylthio, arylthio or $NR^6R^7$;
- $R^6$ and $R^7$ may be the same or different and are selected from hydrogen, alkyl, aryl, $COR^8$ or $SO_2R^8$;
- $R^8$ is alkyl, aryl, alkoxy or aryloxy;
- n is 1 or 2;
- $R^9$ is alkyl, aryl or $NR^{10}R^{11}$; and
- $R^{10}$ and $R^{11}$ may be the same or different and are selected from hydrogen, alkyl or aryl.

In formula (I), halogen (or halo) includes chloro, bromo and fluoro and the alkyl and alkoxy groups and moieties each have from 1 to 4 carbon atoms. Certain compounds of formula (I) may exist in their solvated forms. The group Ar in formula (I) is preferably unsubstituted or has substituents selected from alkyl (preferably methyl) and/or halogen (preferably chloro) and/or hydroxy grops. As Ar in formula (I), the group 2,3-dimethylphenyl is particularly preferred. Preferably $R^6$ is hydrogen and $R^7$ is phenyl or benzoyl.

The term "aryl" as used herein includes phenyl or naphthyl either unsubstituted or substituted with one or more substituents, the substituent(s) being the same or different and preferably selected from alkyl, alkoxy, halogen, nitro, hydroxy, cyano, carbalkoxy and amino.

The compounds of formula (I) and their acid addition salts have activity against Arthropods, in particular against members of the order Acarina. The compounds of formula (I) may be used to control pests such as *Rhipicephalus appendiculatus, Boophilus decoloratus, Boophilus microplus, Rhipicephalus evertsi, Amblyomma hebraeum, Psoroptes ovis* and Hyalomma species on animals and Tetranychus species on plants.

The compounds of formula (I) may be prepared by any known method for the preparation of known compounds of an analogous structure.

In particular the compounds of formula (I) may be prepared from 2-substituted imidazolines of formula (II) or an acid addition salt thereof:

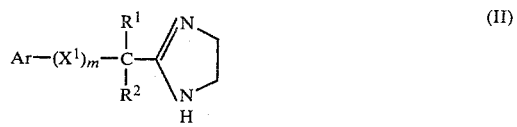
(II)

wherein Ar, $X^1$, m, $R^1$ and $R^2$ are as defined above, either by a direct addition reaction with an isocyanate or isothiocyanate (e.g. phenylisocyanate (to give a compound of formula (I) where $Z^2$ is an N-substituted carbamoyl or thiocarbamoyl group); a ketone (to give a compound of formula (I) where $Z^2$ is an acyl group) or a carbodiimide (to give a compound of formula (I) where $Z^2$ is an amidine); or by a substitution reaction with a compound of formula (III):

$$Z^2-X'$$ (III)

wherein $Z^2$ is as defined above and X' is a leaving group such as halo (e.g. in acid chlorides or haloformate esters), acyl (e.g. in acid anhydrides), alkoxy or alkylthio (e.g. carbamates, imidates, thiocarbamates or thioimidates) or sulphonyloxy (e.g. in mixed anhydrides).

In one particular application of the above substitution reaction, compounds of formula (I) wherein $Z^2$ is a thiocarbamoyl group may be prepared by the reaction of a compound of formula (II) with a compound of formula (III) wherein $Z^2$ is a thiocarbamoyl group and X' is $NH_2$ (i.e. $Z^2-X'$ is a thiourea).

The reaction may be effected optionally in water or an organic solvent, such as chloroform or methylene chloride, preferably in the presence of a base, such as an alkali metal hydroxide, an alkali metal carbonate, or a tertiary organic base, such as triethylamine, pyridine or substituted pyridines or piperidines, such as tetramethylpiperidine or pentamethylpiperidine; and generally at temperatures of from $-70°$ C. to $120°$ C., preferably at temperatures of from $-10°$ C. to $40°$ C.

Compounds of formula (I), in particular where $Z^2$ is not a strongly electron-withdrawing group, may be prepared by reacting an ethylenediamine of formula (IV) or salt thereof:

(IV)

wherein $Z^2$ is as defined hereinabove, with an appropriate carboxylic acid or a reactive derivative thereof such as imidate, thioimidate, acid halide, acid anhydride, imidohalide, ester, amidine, thioamide, amide or nitrile. These reactants may be conveniently represented by formula (V):

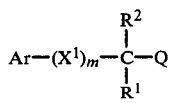

(V)

wherein Ar, $X^1$, m, $R^1$ and $R^2$ are as defined hereinabove and Q is a carboxyl group or a reactive derivative thereof which produces the imidazoline ring structure of formula (I) when reacted with a compound of formula (IV).

Suitable reactive derivatives are:

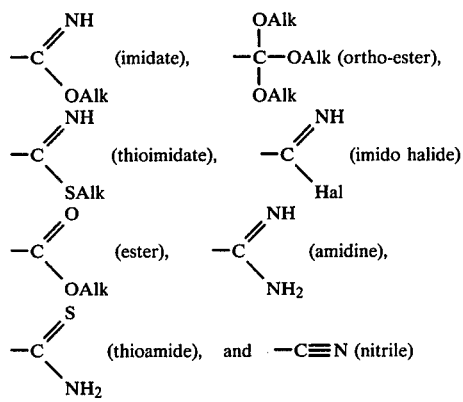

wherein 'Alk' is an alkyl group having from 1 to 6 carbon atoms.

The conditions under which this reaction may be carried out depend upon the nature of the starting materials used, and a liquid medium may be present or absent; high and low temperatures may be used, and various pressures employed.

When the carboxylic acid derivative is an imidate, this is preferably in the form of an acid addition salt such as a hydrogen halide salt, and may be prepared from the nitrile and a suitable anhydrous alkanol, such as ethanol or methanol, in the presence of dry diethyl ether or chloroform and hydrogen chloride at a low temperature. The reaction may be carried out at a temperature in the range of −20° C. to ambient temperature. The reaction with an ethylenediamine of formula (IV) is conducted in an inert anhydrous medium such as chloroform, methylene chloride or ether. The reactants are preferably heated under reflux until reaction is complete.

The nitrile referred to in the reaction just described may be prepared from a compound of formula:

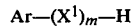

in which Ar and $X^1$ are as defined for formula (I) and m is 1 by reaction with formaldehyde or an adduct thereof decomposable to formaldehyde, e.g. the sodium metabisulphite adduct, in the presence or absence of a solvent, such as absolute ethanol, at an elevated temperature, e.g. 100° C. The product of this reaction is then reacted, usually without isolation, with a solution of an inorganic cyanide, e.g. potassium cyanide. These reactions have been described by, for example, Warunis and Sachs, Berichte, Volume 37, page 2636 and Bucherer Berichte, Volume 37, page 2825.

The thioimidate intermediates in the form of acid addition salts may be prepared from the corresponding nitrile (prepared for example as just described) by reaction with an alkyl mercaptan and a hydrogen halide gas at a low temperature of about 0° C., in the presence of dry diethyl ether. The thioimidate may then be reacted with an ethylenediamine of formula (IV), the reaction being effected at the reflux temperature of the reaction mixture.

The acid halide, ester and anhydride intermediates may be conveniently prepared from the corresponding acid by known methods, and the acid itself may be prepared from the corresponding nitrile (prepared for example as described above). They may then be reacted with an ethylenediamine of formula (IV), preferably in the presence of a liquid medium which may be polar or non-polar. The reaction is preferably carried out at an elevated temperature.

The compounds of formula (I) may be prepared from the imidohalide intermediates by reaction with an ethylenediamine of formula (IV), under anhydrous conditions in the presence or absence of an acid acceptor and optionally at an elevated temperature. The reaction mixture may include a polar or non-polar liquid medium such as a lower alkanol or an ether.

The amidine intermediate in the form of the base or acid addition salts thereof, is preferably converted to a compound of formula (I) by heating under reflux with an ethylenediamine of formula (IV) in the presence of a polar or non-polar liquid medium, for example a lower alkanol, until ammonia ceases to be evolved. Alternatively, ethylene dichloride or 2-chloroethylamine may be used in place of ethylenediamine. The amidine intermediates themselves may be prepared by any known method, but conveniently from the corresponding imidates by reaction with ammonia.

The thioamide and amide intermediates may be prepared from the corresponding nitriles or by any other convenient method and may be converted into compounds of formula (I) by heating with an ethylenediamine of formula (IV), at a reflux or higher temperature, in the presence or absence of a polar or non-polar solvent. Conveniently, the reactions are partly effected under reduced pressure to induce the removal of ammonia and/or hydrogen sulphide from the reaction mixture.

The nitrile intermediates may be reacted in the presence or absence of a liquid medium with an ethylenediamine of formula (IV) or a salt thereof; the reaction may be carried out in the presence of hydrogen sulphide. A liquid medium such as a lower alkanol may be included in the reaction mixture which may be heated to reflux temperature, or to a higher temperature in a closed vessel, optionally in the presence of an inert gas such as nitrogen.

It will of course be understood that, where the intermediate is the carboxylic acid, the acid halide, ester, amide or thioamide, there may be isolated as an intermediate the acylethylenediamines of formula (VI):

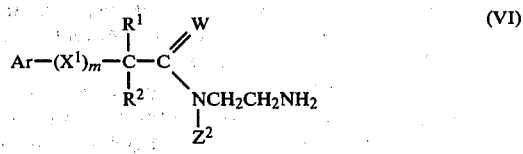

(VI)

wherein Ar, $X^1$, m, $R^1$, $R^2$ and $Z^2$ are as defined above and W is oxygen or sulphur and these compounds may themselves be converted in situ to a compound of formula (I), either by separate treatment with a dehydrating agent, such as calcium oxide, or by continuing the reaction to completion under the original conditions to give rise to a compound of formula (I).

The compounds of formula (I) where m is 1 may be prepared by the reaction of a compound of formula (VII), or an N- or S-metal compound thereof;

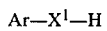  (VII)

wherein Ar and $X^1$ are as defined in formula (I) (m is one), with a reactive ester derivative of formula (VIII):

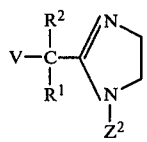  (VIII)

wherein $R^1$, $R^2$ and $Z^2$ are as defined in formula (I), and V is a leaving group derived from a suitable inorganic or organic acid. Suitable derivatives are halo, such as chloro, iodo, or bromo, alkylsulphonyloxy or arylsulphonyloxy such as p-toluenesulphonyloxy.

The reactive ester derivatives of formula (VIII) may be in the form of their bases or acid addition salts thereof. The reaction is carried out in an inert liquid medium which is preferably a polar liquid such as acetonitrile or isopropanol, or may be dimethylsulphoxide, sulpholane, methyl ethyl ketone, dimethylformamide, acetone, dimethylacetamide, N-methyl-2-pyrrolidone, or mixtures of the foregoing. In the case where V is chloro in a compound of formula (VIII), then a small catalytic quantity of an iodide salt, such as sodium iodide, or a phase transfer catalyst such as a quaternary ammonium salt, for example benzyltrimethyl ammonium chloride, may advantageously be included in the reaction mixture. The reactants may be heated together under an inert atmosphere, such as nitrogen, at the reflux temperature of the reaction mixture.

The compounds of formula (I) in which Z is

may also be prepared by reacting a compound of formula (IX):

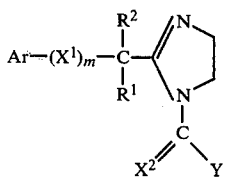  (IX)

in which Ar, $X^1$, $X^2$, $R^1$, $R^2$ and m are as defined for formula (I) and Y is a leaving group (such as halo, acyl, alkoxy, alkylthio, $S^-$, SH, sulphonyloxy or carbalkoxy) with a suitable active-hydrogen containing a compound of formula (X):

  (X)

wherein $R^{12}$ is alkoxy, aryloxy or $NR^6R^7$ and $R^6$ and $R^7$ are as defined above.

In one particular aspect this method may be applied to the preparation of compounds of formula (I) in which $Z^2$ is a carbamoyl group by treatment of compound (IX) in which Y is SR" and $X^2$ is $NR^5$ when $R^5$ is as defined above and R" is an alkyl group with a suitable active-hydrogen containing compound of formula (X) above. The intermediate compounds of formula (IX) in which Y is —SR" and $X^2$ is $NR^5$ may be prepared from compounds of general formula (XI):

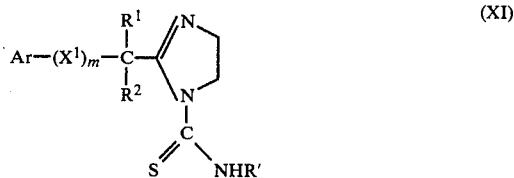  (XI)

wherein Ar, $X^1$, m, $R^1$ and $R^2$ are as defined for formula (I) and R" is as defined above.

The compounds of formula (I), wherein $Z^2$ is

$R^4$ is as defined above and $X^2$ is $NR^5$ where $R^5$ is as defined in formula (I) above, may also be prepared by reacting a compound of formula (II) above with an imidoyl dihalide of formula (XII):

  (XII)

wherein
 $R^5$ is as defined in formula (I) above and Hal is chloro, bromo or iodo;
 to give an intermediate of formula (IX) above wherein $X^2$ is $R^5$—N and Y is Hal.

Compounds of formula (I) in which m is 1 and $X^1$ is $NR^3$ or $NZ^1$, $R^3$ and $Z^1$ being as defined for formula (I), may be prepared by reacting a compound of formula:

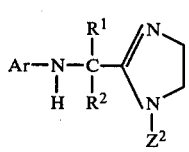  (XIV)

wherein Ar, $R^1$, $R^2$ and $Z^2$ are as defined for formula (I) with a compound of formula

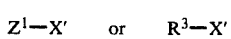

wherein $Z^1$ and $R^3$ are as defined for formula (I) and X' is as defined and exemplified for formula (III) above. The reaction may be carried out under the conditions described above for the reaction between a compound of formula (II) and a compound of formula (III), although generally the reaction is less readily carried out, especially when the compound of formula $R^3$—X' is used.

The compounds of formula (I) may be isolated from the reaction mixture as the free base or in the form of an acid addition salt. The bases may be converted into acid addition salts thereof by known techniques with the aid of the appropriate acid, and salts of the compound may also be converted into the free bases or into other acid addition salts.

For use as a pesticide, the compounds of formula (I) may be presented in the form of their free bases, or as acid addition salts thereof. Suitable salts of formula (I) include hydrohalide e.g. hydrochloride, sulphate, nitrate, phosphate, thiocyanate, acetate, propionate, stearate, naphthenate, perchlorate, benzoate, methanesulphonate, ethanesulphonate, tosylate and benzenesulphonate acid addition salts thereof.

The compounds of formula (I) may be used to combat insects, ticks, mites and other arthropods including free-living arthropods and those which are ectoparasites of plants, mammals and birds and may be used alone or in combination with an additive which may take the form of one or more of the carriers used in the formulation art: wetting, diluting, stabilising, thickening, emulsifying, dispersing or surface active agents, or other standard carrier ingredients.

A formulation may be an aqueous solution of an acid addition salt of a compound of formula (I), or a suspension of a compound of formula (I) in water, and may be used alone or in combination with suitable surface active agents. The formulation per se may be used alone or diluted in water for application to the pests or their immediate environment by way of spraying or dipping.

A formulation may be in the form of a miscible oil comprising a compound of formula (I) in the form of its free base or with an equimolar quantity of a suitable organic acid, such as oleic acid or naphthenic acid, to provide a salt soluble in organic solvents, and emulsifiers, and the formulation may be applied as an emulsion by way of spraying or dipping.

A formulation may be a non-aqueous solution or suspension of a compound of formula (I) in a suitable organic solvent for the direct application by the "pour-on" method. A formulation may also take the form of a wettable powder for dilution with water and application by dipping or spraying. Other solid formulations may also be used for direct application without dilution, such as dusts, powders and granules. A further formulation may be a paste, grease or gel containing a compound of formula (I) and a suitable carrier, and may be applied by spreading the formulation over the infested area.

An acid addition salt or base of a compound of formula (I) is preferably present in a pesticidal formulation in an amount of from 5 to 80%, calculated by weight of the base, and particularly preferred formulations contain about 20%, calculated by weight of the base. The concentration of a compound of formula (I) applied to the pests or their immediate environment may be in the range of from 0.001% to 20%, calculated by weight of the base.

The present invention accordingly provides any novel feature described herein, principally but not exclusively, for example:

(a) a novel substituted imidazoline compound of formula (I) or an acid addition salt thereof;
(b) a method of preparation of a novel compound of formula (I) or an acid addition salt thereof;
(c) a method of controlling arthropod pests, particularly members of the Order Acarina, comprising the application to the pests or the pest's environment of a compound of formula (I);
(d) a pesticidal formulation comprising a compound of formula (I) and a carrier therefor;
(e) a method of making a formulation comprising an admixture of a carrier and a compound of formula (I).

The following Examples are provided by way of illustration of the present invention and should not be construed as in any way constituting a limitation thereof.

EXAMPLE 1

1-N-Phenylcarbamoyl-2-(3,4-dimethylbenzyl)-2-imidazoline 2-(3,4-Dimethylbenzyl)-2-imidazoline hydrochloride (3.43 g; 0.01 mole) was suspended in dry chloroform (50 ml). The so obtained mixture was treated with tetramethylpiperidine (1.41 g; 0.01 mole) in dry chloroform (20 ml) and stirred at ambient temperature for approximately 4 hours with intermittent shaking, any large pieces of solid being broken up by means of a glass rod. Phenylisocyanate (1.20 g; 0.01 mole) in dry chloroform (10 ml) was then added dropwise to the cooled reaction mixture and the resulting mixture stirred overnight at ambient temperature. The solvent was evaporated under reduced pressure, the residue shaken up with water (60 to 100 ml) and filtered. The white solid so obtained was then transferred to a vacuum dessicator over fresh potassium hydroxide and left until the material had a constant melting point, to give 1-N-phenylcarbamoyl-2-(3,4-dimethylphenyl)-2-imidazoline, m.p. 139°–142° C. The $^1$H NMR spectrum was consistent with the assigned structure.

EXAMPLE 2

(a) 2-Phenylthiomethyl-2-imidazoline

O-ethyl phenylthioacetamidate (23.15 g; 0.10 mole) in dry ethanol (50 ml) was treated at 0° C. with dry ethylenediamine (6.6 g; 0.11 mole) in ethanol (10 ml) with stirring over ½ hour. The mixture was then refluxed for 6 hours, cooled and evaporated in vacuo to an oil. This oil was treated with ice and 2 N NaOH (60 ml, 0.12 mole) and the alkaline mixture extracted with chloroform. After drying over $MgSO_4$ the extracts were evaporated to give 18 g of an orange solid which was recrystallised from diisopropyl ether to give a solid, m.p. 84.0° to 85.6° C.

(b) 1-N-Phenylcarbamoyl-2-phenylthiomethyl-2-imidazoline

2-Phenylthiomethyl-2-imidazoline (4.8 g; 0.025 mole) was dissolved in $CH_2Cl_2$ (200 ml) and the solution cooled to −15° C. before treating dropwise with fresh phenyl isocyanate (3.0 g; 0.025 moles) over 15 minutes. The mixture was allowed to warm to room temperature and stirring continued for a further 2 hours. The solvent was then evaporated in vacuo and the residue recrystallised from ethyl acetate, to give a solid, m.p. 117.4° to 119.0° C.

EXAMPLE 3

1-N-Phenylthiocarbamoyl-2-(N''-(2-hydroxyphenyl)-3-toluidinomethyl)-2-imidazoline 2-(N''-(2-hydroxyphenyl)-3-toluidinomethyl)-2-imidazoline methane sulphonate, (0.908 g; 2.40×10$^{-3}$ mole) was suspended in dry $CHCl_3$ (50 ml) at 0° C.

Tetramethylpiperidine (0.339 g; 2.40×10$^{-3}$ mole) was added to the stirred cooled suspension and stirring continued for a further ½ hour. Fresh phenyl isothiocyanate (0.325 g; 2.73×10$^{-3}$ mole) in dry CHCl$_3$ (15 mls) was then added cautiously to the cooled suspension and the resulting mixture stirred at 0° C. for a further 2 hours. The mixture was allowed to rise to room temperature overnight. The solvent was then evaporated, dry ethanol (30 ml) added to the residue and the mixture filtered. The filtrate was treated with enough hexane to produce a second crystalline precipitate. This precipitate was removed by filtration and the process repeated with addition of small quantities of hexane to each successive filtrate until continued addition of hexane produced no further solid. The solid fractions were dried in vacuo and labelled 1 to 5. Fractions 4 and 5 showed a single spot on thin layer chromatography and gave a proton NMR spectrum consistent with the postulated structure. Fractions 4 and 5 had m.p. 66.8° to 68.4° C.

EXAMPLE 4

(a) Preparation of N-cyanomethyl, N-methylaniline

N-methylaniline (40.0 g; 0.373 mole) chloroacetonitrile (28.2 g; 0.373 mole), phenol (21.08 g; 0.224 mole) and sodium iodide (2.0 g, catalytic trace) were refluxed together at 140° C. oil bath temperature for 2 hours. The solid residue on cooling was extracted with Et$_2$O/NaOH and the ethereal layer washed with water, dried over MgSO$_4$ and then evaporated. The residue was distilled under vacuum and the fraction distilling at 147° to 151° C./13 mmHg was shown by NMR to be the required product.

(b) Preparation of O-ethyl-(N-methylanilino)acetimidate hydrochloride

N-cyanomethyl, N-methylaniline (18.0 g; 0.123 mole) was dissolved in 180 ml dry ether and 8.5 ml (0.146 mole) dry ethanol and the solution cooled in an ice bath. Dry HCl gas was passed into the stirred solution until this was saturated and the mixture then left at 0° C. for 48 hours. The precipitate obtained was filtered, washed with dry ether and stored in a vacuum dessicator.

(c) Preparation of 2-(N-methylanilinomethyl)-2-imidazoline

O-ethyl-2-(N-methylanilino)acetimidate hydrochloride (9.8 g; 0.0429 mole) was refluxed for 2½ hours with 5.24 g;(0.087 mole) dry ethylenediamine in super dry ethanol (50 ml). The solvent was removed and the residue washed with 10% aqueous Na$_2$CO$_3$/CHCl$_3$ and the organic extract was washed with water, dried over MgSO$_4$ and then, after evaporation of the solvent, recrystallised from CH$_2$Cl$_2$/Diisopropyl ether to give a solid, m.p.

(d) Preparation of 1-N-benzoylcarbamoyl-2-(N''-methyl anilinomethyl)-2-imidazoline 2-(N'-methylanilinomethyl)-2-imidazoline (3.1 g; 0.0164 mole) was dissolved in dry CHCl$_3$ (35 mls) at 0° C. Benzoyl isocyanate (2.41 g; 0.0164 mole) was dissolved in 10 mls dry CHCl$_3$ and added dropwise to the stirred mixture at 0° C. After addition was complete, the reaction was stirred at 0° C. for a further 2 hours and then allowed to warm to room temperature overnight. The solvent was removed, the residue washed with cold CH$_2$Cl$_2$ and the NMR spectrum of the remaining solid found to be consistent with that expected for the desired product. The solid had a m.p.

EXAMPLE 5

Engorged female ticks of the Biarra Strain of *Boophilus microplus* are immersed, in groups of 20 ticks, per concentration in a range of dilutions of the compound under test. The wash is prepared immediately prior to the test by dilution (with water) of the compound under test. The constituents may be in the form of miscible oil or wettable powder formulations. The desired range of concentrations for the test is obtained by further dilution of the master solution or wash.

The ticks are removed from the wash after 10 minutes, dried, and stuck dorsal down on double-sided adhesive tape. They remain in this position for 14 days when the numbers laying viable eggs are determined, and recorded as IRx values (% concentrations at which x% inhibition of egg-production occurs).

The results obtained are shown in Table 1.

TABLE 1

| Compound | Ex. No. | IR |
|---|---|---|
| 1-N-phenylcarbamoyl-2-(3,4-dimethylbenzyl)-2-imidazoline | 1 | IR20 - 0.2% |

EXAMPLE 6

Test compounds were formulated in polyethyleneglycol and injected into ticks at a site just ventral to the mouth parts. After 14 days the percentage inhibition of egg production (IR) was determined. The results are shown in Table 2.

TABLE 2

| Compound | Ex. No. | % IR |
|---|---|---|
| 1-N-phenylcarbamoyl-2-phenylthiomethyl-2-imidazoline | 2(b) | 100% at 10 mg/ml |
| 1-N-phenylcarbamoyl-2-(3,4-dimethylbenzyl)-2-imidazoline | 1 | 70% at 1.0 mg/ml |

The following formulations are given to illustrate the way in which the pesticidal compounds of the invention can be applied to pests or environments susceptible to pest attack.

FORMULATION 1
Dusting Powders

| Active Compound | 1.0 | 20.0 | parts by weight |
|---|---|---|---|
| Talc | 99.0 | 80.0 | parts by weight |
|  | 100.0 | 100.0 | |

FORMULATION 2
Wettable Powder

| Active Compound | 25.0 parts by weight |
|---|---|
| Sodium Dioctyl Sulphosuccinate | 1.0 parts by weight |
| Dispersol ACA | 2.0 parts by weight |
| Kaolin | 72.0 parts by weight |
|  | 100.0 |

FORMULATION 3
Aqueous Dispersion

| Active Compound | 20.0 parts by weight |
|---|---|
| Keltrol | 0.4 parts by weight |
| Sodium Dioctyl Sulphosuccinate | 0.5 parts by weight |
| Water | 79.1 parts by weight |
|  | 100.0 |

FORMULATION 4

-continued

| Pour-On | |
|---|---|
| Active Compound | 5.0 parts by weight |
| Dimethyl Formamide | 85.0 parts by weight |
| Castor Oil | 10.0 parts by weight |
| | 100.0 |

| FORMULATION 5 Grease | |
|---|---|
| Acitive Compound | 6.0 parts by weight |
| Petroleum Jelly | 94.0 parts by weight |
| | 100.0 |

| FORMULATION 6 Miscible Oil | |
|---|---|
| Active Compound | 10.0 parts by weight |
| Aromasol H | 70.0 parts by weight |
| Nonyl Phenol Ethoxylate | 20.0 parts by weight |
| | 100.0 |

What is claimed is:

1. An imidazoline compound of formula (I):

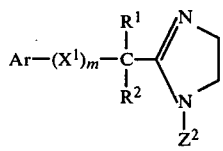

wherein
Ar is selected from a phenyl or a mono-, di- or tri-substituted phenyl radical in which the substituents may be the same or different and are selected from alkyl, alkoxy, halogen, hydroxy, cyano, amino, trihalomethyl and nitro and in which any two adjacent, otherwise unsubstituted, carbon atoms of the phenyl ring may together be joined by a carbon chain containing 3 or 4 carbon atoms;
$X^1$ is S;
$R^1$ and $R^2$ may be the same or different and are selected from hydrogen or alkyl;
m is 0 or 1; and
$Z^2$ is a group $SO_nR^9$ or a group

in which $X^2$ is O, S or $NR^5$;
$R^4$ is alkyl, aryl, alkoxy, aryloxy or $NR^6R^7$;
$R^5$ is alkyl, aryl, alkoxy, aryloxy, alkylthio, arylthio or $NR^6R^7$;
$R^6$ and $R^7$ may be the same or different and are selected from hydrogen, alkyl, aryl, $COR^8$ or $SO_2R^8$;
$R^8$ is alkyl, aryl, alkoxy or aryloxy;
n is 1 or 2;
$R^9$ is alkyl, aryl or $NR^{10}R^{11}$; and
$R^{10}$ and $R^{11}$ may be the same or different and are selected from hydrogen, alkyl or aryl, the above mentioned alkyl or alkoxy radicals or moieties containing from 1 to 4 carbon atoms each; the imidazoline compound being the free base or present as an acid addition salt thereof, and in the above aryl is phenyl or naphthyl either unsubstituted or substituted with one or more substituents, the substituents being the same or different and selected from the group consisting of alkyl, alkoxy, halogen, nitro, hydroxy, cyano, carbalkoxy and amino.

2. An imidazoline compound of formula (1):

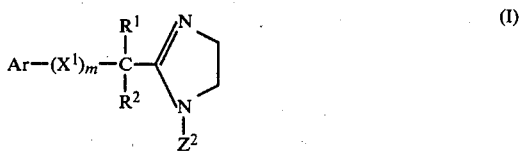

wherein
Ar is selected from a phenyl or a mono-, di- or tri-substituted phenyl radical in which the substituents may be the same or different and are selected from alkyl, alkoxy, halogen, hydroxy, cyano, amino, trihalomethyl and nitro and in which any two adjacent, otherwise unsubstituted, carbon atoms of the phenyl ring may together be joined by a carbon chain containing 3 or 4 carbon atoms;
$X^1$ is S: $R^1$ and $R^2$ may be the same or different and are selected from hydrogen or alkyl;
m is 1; and
$Z^2$ is a group

in which $X^2$ is O or S;
$R^4$ is $NR^6R^7$;
$R^6$ and $R^7$ may be the same or different and are selected from hydrogen, alkyl, aryl, $COR^8$ or $SO_nR^8$;
$R^8$ is alkyl, aryl, alkoxy or aryloxy;
n is 1 or 2; and the alkyl or alkoxy radicals or moieties containing from 1 to 4 carbon atoms, each; the imidazoline compound being the free base or present as an acid addition salt thereof, and in the above aryl is phenyl or naphthyl either unsubstituted or substituted with one or more substituents, the substituents being the same or different and selected from the group consisting of alkyl, alkoxy, halogen, nitro, hydroxy, cyano, carbalkoxy and amino.

3. A compound according to claim 1 wherein Ar is selected from the group consisting of unsubstituted phenyl and substituted phenyl having one, two or three substituents which are the same or different and are alkyl, halogen or hydroxy.

4. A compound according to claim 1 wherein Ar is substituted phenyl having one, two or three substituents which are the same or different and are alkyl or halogen.

5. A compound according to claim 4 in which Ar is substituted phenyl wherein the substituent(s) is/are selected from methyl and chloro.

6. A compound according to claim 1 wherein Ar is di-substituted phenyl.

7. A compound according to claim 6 wherein Ar is 2,3-dimethylphenyl.

8. A compound according to claim 1 wherein $Z^2$ is a group

where $X^2$ and $R^4$ are as defined in claim 1.

9. A compound according to claim 8 wherein $Z^2$ is a group

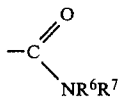

where $R^6$ and $R^7$ are as defined in claim 1.

10. A compound according to claim 8 wherein $Z^2$ is

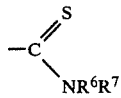

where $R^6$ and $R^7$ are as defined in claim 1.

11. A compound according to claim 8 wherein $R^4$ is $NR^6R^7$, $R^6$ is hydrogen and $R^7$ is aryl or —COaryl.

12. A compound according to claim 11 wherein $R^7$ is selected from the group consisting of phenyl and benzoyl.

13. 1-N-Phenylcarbamoyl-2-(2,3-dimethylbenzyl)-2-imidazoline or an acid addition salt thereof.

14. 1-N-Phenylcarbamoyl-2-phenylthiomethyl-2-imidazoline or an acid addition salt thereof.

15. A pesticidal formulation comprising, as active ingredient an effective pesticidal amount of, a compound of formula (I) as defined in claim 1 or an acid addition salt thereof together with a carrier therefor.

16. A pesticidal formulation according to claim 15 wherein the active ingredient is present in an amount of from 5 to 80%, calculated by weight of the base.

17. A pesticidal formulation according to claim 16 wherein the active ingredient is present in an amount of about 20%, calculated by weight of the base.

18. A pesticidal formulation according to claim 15 in the form of a wettable powder.

19. A pesticidal formulation according to claim 15 wherein the active ingredient is 1-N-phenylcarbamoyl-2-(2,3-dimethylbenzyl)-2-imidazoline or an acid addition salt thereof.

20. A pesticidal formulation according to claim 15 wherein the active ingredient is 1-N-phenylcarbamoyl-2-phenylthiomethyl-2-imidazoline or an acid addition salt thereof.

21. A method of controlling arthropod pests which comprises applying to the pest or the pest's environment an effective pesticidal amount of a compound of formula (I) as defined in claim 1 or 2.

22. A method according to claim 21 wherein the compound is applied at a concentration of 0.001% to 20%, calculated by weight of the base.

23. A method according to claim 21 wherein the pest is a member of the order Acarina.

* * * * *